United States Patent [19]

Pitner et al.

[11] Patent Number: 5,691,145
[45] Date of Patent: Nov. 25, 1997

[54] DETECTION OF NUCLEIC ACIDS USING G-QUARTETS

[75] Inventors: J. Bruce Pitner, Durham; Glenn P. Vonk, Fuquay-Varina; James G. Nadeau, Chapel Hill, all of N.C.

[73] Assignee: Becton, Dickinson and Company, Franklin Lakes, N.J.

[21] Appl. No.: 703,755

[22] Filed: Aug. 27, 1996

[51] Int. Cl.$^6$ .............................. C12Q 1/68; C12P 19/34; C07H 21/04; C07H 21/02
[52] U.S. Cl. .................. 435/6; 435/91.1; 536/24.3; 536/23.1; 436/94; 436/800; 436/805
[58] Field of Search ........................... 435/5, 6, 91.1, 435/91.5; 536/24.3, 23.1; 436/94, 800, 805

[56] References Cited

U.S. PATENT DOCUMENTS

| 4,996,143 | 2/1991 | Heller et al. | 435/6 |
| 5,523,389 | 6/1996 | Ecker et al. | 536/23.1 |
| 5,538,848 | 7/1996 | Livak et al. | 435/5 |

FOREIGN PATENT DOCUMENTS

| 0601889 | 6/1994 | European Pat. Off. | C12Q 1/68 |

OTHER PUBLICATIONS

L. E. Morrison and L. M. Stols "Sensitive Fluorescence–Based Thermodynamic and Kinetic Measurements of DNA Hybridization in Solution" Biochem. 32:3095–3104 (1993).
K. M. Parkhurst and L. J. Parkhurst "Kinetic Studies by Fluorescence Resonance Energy Transfer Employing a Double–Labeled Oligonucleotide: Hybridization to the Oligonucleotide Complement and to Single–stranded DNA" Biochem. 34:285–292 (1995).
J. P. Cooper and P. J. Hagerman "Analysis of Fluorescence Energy Transfer in Duplex and Branched DNA Molecules" Biochem. 29:9261–9268 (1990).
L. B. McGown, et al. "The Nucleic Acid Ligand—A New Tool for Molecular Recognition" Anal. Chem. Nov. 1, 1995, pp. 663A–668A.
M. F. Kubik, et al. "High–affinity RNA ligands to human α–thrombin" Nucl. Acids Res. 22:2619–2626 (1994).
W. Bannwarth, et al. "Energy Transfer within Oligonucleotides from a Lumazine (=Pteridine–2,4(1H,3H)–dione) Chromophore to Bathophenanthroline–ruthenium(II) Complexes" Helv. Chim. Acta 74:1991–1999 (1991).
J–L. Mergny, et al. "Fluorescence Energy Transfer between Two Triple Helix–Forming Oligonucleotides Bound to Duplex DNA" Biochem. 33:15321–15328 (1994).
R. A. Cardullo, et al. "Detection of nucleic acid hybridization by nonradiative fluorescence resonance energy transfer" Proc. Natl. Acad. Sci. USA 85:8790–8794 (1988).
E. Dias, et al. "Chemical Probe for Glycosidic Conformation in Telomeric DNAs" J. Am. Chem. Soc. 116:4479–4480 (1994).
K. Y. Wang, et al. "A DNA Aptamer Which Binds to and Inhibits Thrombin Exhibits a New Structural Motif for DNA" Biochem. 32:1899–1904 (1993).
R. F. Macaya, et al. "Thrombin–binding DNA aptamer forms a unimolecular quadruplex structure in solution" Proc. Natl. Acad. Sci. USA 90:3745–3749 (1993).
P. Schultze, et al. "Three–dimensional Solution Structure of the Thrombin–binding DNA Aptamer d(GGTTGGTGTGGTTGG)" J. Mol. Biol. 235:1532–1547 (1994).
J. A. Kelly, et al. "Reconciliation of the X–ray and NMR Structures of the Thrombin–Binding Aptamer d(GGTTGTGTGGTTGG)" J. Mol. Biol. 256:417–422 (1996).
L. C. Bock, et al. "Selection of single–stranded DNA molecules that bind and inhibit human thrombin" Nature 355:564–566 (1992).
Abdul–Manan et al. (1996) Biochemistry 35:3545–3554.
Wyatt et al. (1996) Biochemistry 35:8002–8008.
Huertas et al. (1996) Biochemistry 35:13125–13135.
Sugimoto et al. (1996) Nucleosides & Nucleotides 15:559–567.
Wolfe et al. (1996) J. Am. Chem. Sos. 118:6301–6302.
Joseph et al. (1996) Biospectroscopy 2:173–183.

*Primary Examiner*—W. Gary Jones
*Assistant Examiner*—Amy Atzel
*Attorney, Agent, or Firm*—Donna R. Fugit

[57] ABSTRACT

Oligonucleotides which form G-quartet structures have been found to be useful in fluorescence assays to detect a selected nucleic acid sequence. When one end of the oligonucleotide is labeled with a donor fluorophore and the other end is labeled with an acceptor dye, the folding of the molecule in the G-quartet structure brings the donor-acceptor pair into close proximity, allowing an interaction between the two labels which results in quenching of donor fluorescence or a change in other fluorescence properties which are the result of the interaction of two dyes in close proximity. The G-quartet structure unfolds upon hybridization to its complementary sequence, increasing the distance between the two dye labels. This results in decreased donor quenching or a change in another proximity-related fluorescence parameter. The associated increase in donor fluorescence intensity or the change in another fluorescence parameter may be monitored as an indication of the presence of a selected nucleic acid sequence. Alternatively, in some cases a decrease in acceptor fluorescence may be monitored as an indication of the presence of the selected nucleic acid sequence when the acceptor is also a fluorophore.

23 Claims, 4 Drawing Sheets

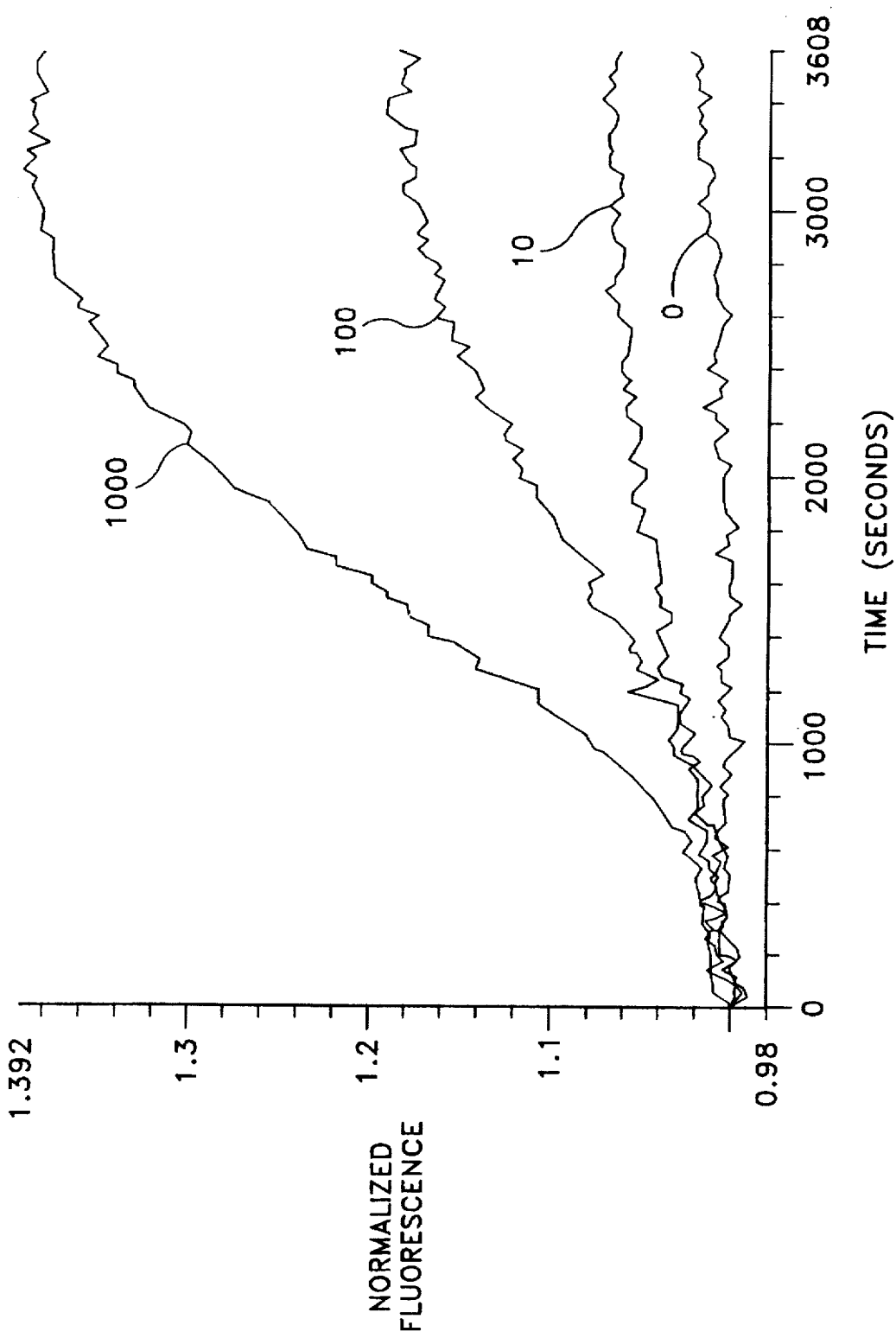

5,691,145

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i x ) FEATURE:
        ( A ) NAME/KEY: misc_feature
        ( B ) LOCATION: 7
        ( D ) OTHER INFORMATION: /standard_name= "N represents N2-5"

( x i ) SEQUENCE DESCRIPTION: SEQ ID NO:1:

GGNTGGNGGN TGG    13

( 2 ) INFORMATION FOR SEQ ID NO:2:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i x ) FEATURE:
        ( A ) NAME/KEY: misc_feature
        ( B ) LOCATION: 3
        ( D ) OTHER INFORMATION: /standard_name= "N represents at
            least two nucleotides"

( i x ) FEATURE:
        ( A ) NAME/KEY: misc_feature
        ( B ) LOCATION: 6
        ( D ) OTHER INFORMATION: /standard_name= "N represents at
            least 2 nucleotides"

( i x ) FEATURE:
        ( A ) NAME/KEY: misc_feature
        ( B ) LOCATION: 9
        ( D ) OTHER INFORMATION: /standard_name= "N represents at
            least two nucleotides"

( x i ) SEQUENCE DESCRIPTION: SEQ ID NO:2:

GGNGGNGGNG G    11

( 2 ) INFORMATION FOR SEQ ID NO:3:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

GGTTGGTGTG GTTGG    15

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

GGTTTTGGTT TTGGTTTTGG    20

( 2 ) INFORMATION FOR SEQ ID NO:5:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

GGTTGGTGTG GTTGGTCTAG AGTCTTCAAA TATCAGAGCT TTACCTAACA A    51

( 2 ) INFORMATION FOR SEQ ID NO:6:

( i ) SEQUENCE CHARACTERISTICS:
        ( A ) LENGTH: 28 base pairs

-continued (B) TYPE: nucleic acid
(C) STRANDEDNESS: single
(D) TOPOLOGY: linear (x i) SEQUENCE DESCRIPTION: SEQ ID NO:6:

TTGTTAGGTA AAGCTCTGAT ATTTGAAG    28

(2) INFORMATION FOR SEQ ID NO:7:

(i) SEQUENCE CHARACTERISTICS:
(A) LENGTH: 44 base pairs
(B) TYPE: nucleic acid
(C) STRANDEDNESS: single
(D) TOPOLOGY: linear (x i) SEQUENCE DESCRIPTION: SEQ ID NO:7:

GGTGGTGTG GTTGGTTTAT CCGTATGGTG GATAACGTCT TTCA    44

DETECTION OF NUCLEIC ACIDS USING G-QUARTETS

FIELD OF THE INVENTION

The present invention relates to materials and methods for detecting nucleic acids and in particular to materials and methods for detecting nucleic acids which employ a measurable change in fluorescence resulting from a change in the distance between two dye labels.

BACKGROUND OF THE INVENTION

Sequence-specific hybridization of oligonucleotide probes has long been used as a means for detecting and identifying selected nucleotide sequences, and labeling of such probes with fluorescent labels has provided a relatively sensitive, nonradioactive means for facilitating detection of probe hybridization. Recently developed detection methods employ the process of fluorescence energy transfer (FET) for detection of probe hybridization rather than direct detection of fluorescence intensity. Fluorescence energy transfer occurs between a donor fluorophore and an acceptor dye (which may or may not be a fluorophore) when the absorption spectrum of one (the acceptor) overlaps the emission spectrum of the other (the donor) and the two dyes are in close proximity. The excited-state energy of the donor fluorophore is transferred by a resonance dipole-induced dipole interaction to the neighboring acceptor. This results in quenching of donor fluorescence. In some cases, if the acceptor is also a fluorophore, the intensity of its fluorescence may be enhanced. The efficiency of energy transfer is highly dependent on the distance between the donor and acceptor, and equations predicting these relationships have been developed by Förster (1948. *Ann. Phys.* 2:55–75). The distance between donor and acceptor dyes at which energy transfer efficiency is 50% is referred to as the Förster distance ($R_o$). Other fluorescence properties may also be dependent on the proximity of a donor and an acceptor, e.g., fluorescence lifetime of the donor and/or acceptor, fluorescence polarization and fluorescence anisotropy.

Energy transfer and other mechanisms which rely on the interaction of two dyes in close proximity to produce a change in a fluorescence property are an attractive means for detecting or identifying nucleotide sequences, as such assays may be conducted in homogeneous formats. Homogeneous assay formats are simpler than conventional probe hybridization assays which rely on detection of the fluorescence of a single fluorophore label, as heterogenous assays generally require additional steps to separate hybridized label from free label. Typically, FET and related methods have relied upon monitoring a change in the fluorecence properties of one or both dye labels when they are brought together by the hybridization of two complementary oligonucleotides. In this format, the change in fluorescence properties may be measured as a change in the mount of energy transfer or as a change in the amount of fluorescence quenching. In this way, the nucleotide sequence of interest may be detected without separation of unhybridized and hybridized oligonudeotides. The hybridization may occur between two separate complementary oligonucleotides, one of which is labeled with the donor fluorophore and one of which is labeled with the acceptor. In double-stranded form there is decreased donor fluorescence (increased quenching) and/or increased energy transfer as compared to the single-stranded oligonucleotides. Several formats for FET hybridization assays are reviewed in *Nonisotopic DNA Probe Techniques* (1992. Academic Press, Inc., pgs. 311–352). Alternatively, the donor and acceptor may be linked to a single oligonucleotide such that there is a detectable difference in the fluorescence properties of one or both when the oligonudeotide is unhybridized vs. when it is hybridized to its complementary sequence. In this format, donor fluorescence is typically increased and energy transfer and quenching are decreased when the oligonucleotide is hybridized. For example, a self-complementary oligonucleotide labeled at each end forms a hairpin which brings the two fluorophores (i.e., the 5' and 3' ends) into close proximity where energy transfer and quenching can occur. Hybridization of the self-complementary oligonucleotide to its complement on a second oligonucleotide disrupts the hairpin and increases the distance between the two dyes, thus reducing quenching. A disadvantage of the hairpin structure is that it is very stable and conversion to the unquenched, hybridized form is often slow and only moderately favored, resulting in generally poor performance. A "double hairpin" scheme is described by B. Bagwell, et al. (1994. *Nucl. Acids Res.* 22:2424–2425). Kramer and Tyagi (1996. *Nature* 14:303–308) describe a hairpin with the detector sequence in a loop between the arms of the hairpin.

Prior art methods may lack efficiency in the energy transfer itself, and it has often been difficult to achieve adequate spectral resolution to detect meaningful changes in fluorescence. In many methods which monitor fluorescence quenching a small amount of hybridization produces only a small decrease in fluorescence which must be detected in the presence of high levels of background. These methods also suffer from lack of detection sensitivity.

Aptamers are DNA or RNA molecules which bind specific molecular targets. Large populations of randomly generated oligonucleotides may be enriched in aptamers by known in vitro selection and amplification processes. Of particular interest is a single-stranded DNA aptamer which binds thrombin (L. C. Bock, et al. 1992. *Nature* 355:564–566). These thrombin binding aptamers were found to contain the conserved consensus sequence GGNTGGN$_{2-5}$GGNTGG (SEQ ID NO:1) and inhibited thrombin-catalyzed fibrin-clot formation. Analysis of the structure of this molecule has revealed a symmetrical structure containing two tetrads of guanosine base pairs connected by three loops (1993. K. Y. Wang, et al. *Biochemistry* 32:1899–1904; 1993. R. F. Macaya, et al. *PNAS* 90:3745–3749; 1994. P. Schultze, et al. *J. Mol. Biol.* 235:1532–1547; 1996. J. A. Kelly, et al. *J. Mol. Biol.* 256:417–422). This characteristic structure is commonly referred to as a "G-quartet" or "G-quadruplex." E. Dias, et al. (1994. *J. Am. Chem. Soc.* 116:4479–4480) report a similar sequence in which the G-quartet structure is maintained when the length of the oligonucleotide between the G pairs is increased.

A fluorophore is a dye or chemical moiety which can be made to fluoresce. This includes dyes which fluoresce in response to chemical treatment, excitation by light or in biological systems.

A donor or donor fluorophore is a fluorophore which has a fluorescence emission spectrum which overlaps the absorption spectrum of another dye or chemical moiety.

An acceptor or acceptor dye is a dye or other chemical moiety which absorbs light emitted by a donor fluorophore.

SUMMARY OF THE INVENTION

It has now been found that oligonucleotides which form G-quartet structures are useful for detection or identification of nucleotide sequences using measurable changes in fluorescence resulting from a change in the distance between two dye labels linked to the G-quartet oligonucleotide (e.g., energy transfer or fluorescence quenching). When one end of the G-quartet is labeled with a donor fluorophore and the other end is labeled with an appropriate acceptor dye, the characteristic structure of the G-quartet brings the donor-acceptor pair into close proximity, resulting in an interaction between the labels which results in quenching of donor fluorescence. Upon hybridization to a complementary oligonucleotide the G-quartet structure unfolds or linearizes. This increases the distance between the two dye labels, resulting in a decrease in their interaction and a decrease in fluorescence quenching (i.e., an increase in donor fluorescence) which may be monitored as an indication of the presence of a selected nucleic acid sequence. If the acceptor dye is also a fluorophore, it may in some cases exhibit a decrease in fluorescence as the G-quartet linearizes and the distance between the donor and acceptor increases. If so, the decrease in fluorescence of the acceptor may also be measured as an indication of the presence of the selected nucleic acid sequence.

DESCRIPTION OF THE DRAWING

FIG. 1 shows the results of Example 2.

FIG. 2 shows the results of Example 3.

FIG. 3 shows the results of Example 4.

FIG. 4 is a graph illustrating the increase in donor fluorescence when the G-quartet, linked to a donor fluorophore and an acceptor dye, is used as a detectable label on a signal primer to detect target amplification in a Strand Displacement Amplification reaction.

DETAILED DESCRIPTION OF THE INVENTION

Figure 1:
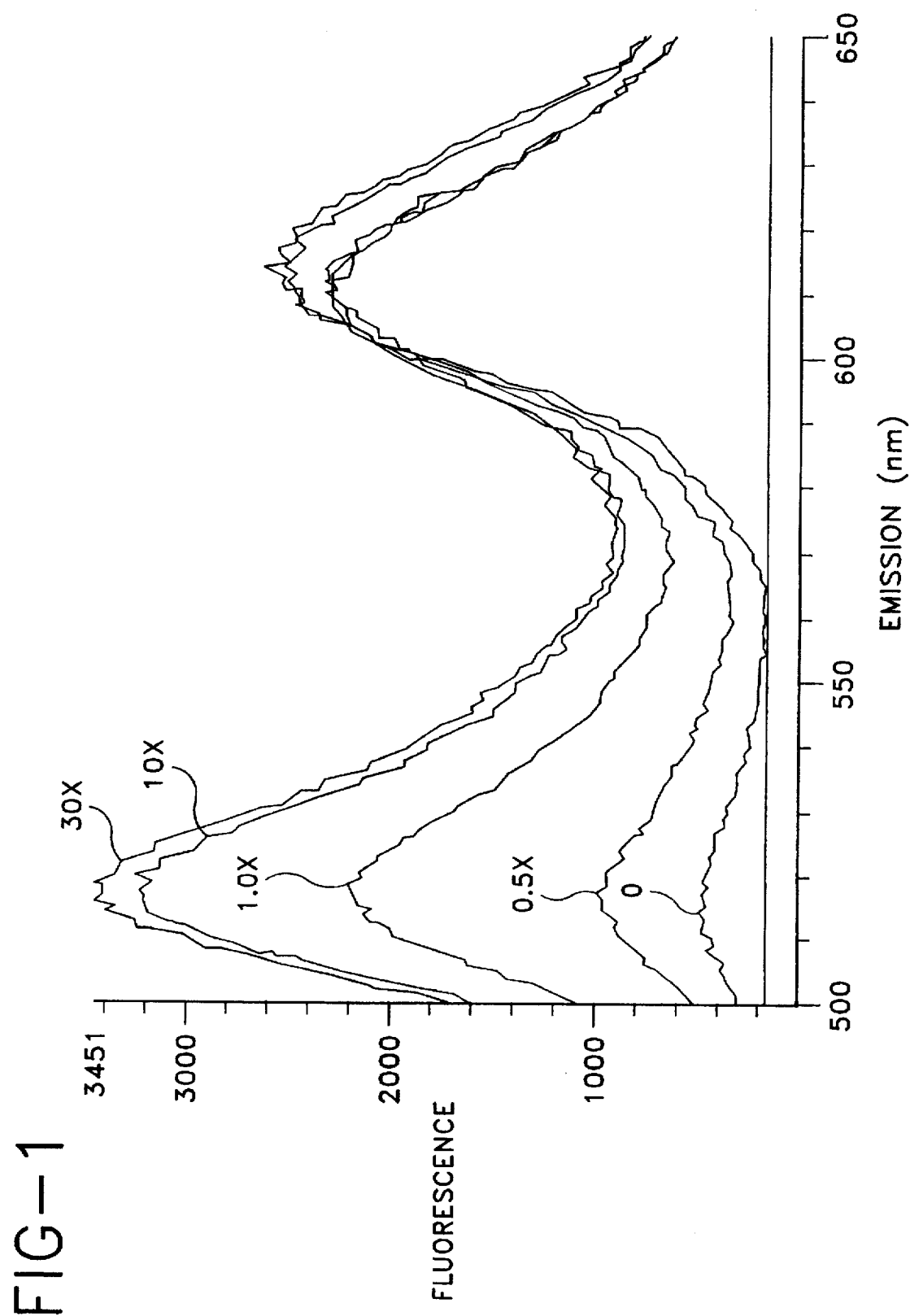
FIG. 1 is a graph illustrating the increase in donor fluorescence observed when a G-quartet hybridizes to its complementary sequence.

G-quartet oligonucleotide structures, when labeled at one end with a donor fluorophore and at the other end with an acceptor dye, provide detector molecules or labels in which fluorescence quenching is unexpectedly efficient. In addition, it was unexpectedly found that the G-quartet structure was rapidly disrupted in the presence of the complementary sequence despite its high stability under normal laboratory conditions. Disruption of the G-quartet structure by unfolding or linearizing is a highly specific indicator of hybridization of the G-quartet oligonucleotide to its complement, as in the absence of the complementary sequence no unfolding or disruption of the structure occurs and fluorescence remains efficiently quenched.

G-quartet oligonucleotides according to one embodiment of the invention have the sequence $GGN_xGGN_yGGN_zGG$ (SEQ ID NO:2), wherein x, y and z indicate a variable number of nucleotides. While x, y and z are each typically at least about 2, preferably about 2–10, these segments may be longer if desired, as they do not effect the proximity of the 5' and 3' end in the folded G-quartet structure, as described below. The G-quartet structure brings the 5' end of the oligonucleotide into close proximity with the 3' end, and for many donor and acceptor dye pairs the distance between them in the G-quartet is less than the Förster distance or otherwise sufficiently close to allow dye-dye interactions which affect the fluorescence intensity of one or both. The relative position of the 5' and 3' ends of the oligonucleotide in the G-quartet structure is therefore the essential feature for using G-quartet oligonucleotides as detector molecules or labels in fluorescence quenching assays, and this proximity is related to the four pairs of G's which are invariant in the oligonucleotide sequence. The regions of variable sequence (i.e., $N_x$, $N_y$, $N_z$) are not critical in the present invention and may be varied in length and sequence without disrupting the characteristic G-quartet structure which gives these molecules their utility in the inventive assays. As a general rule, the variable N sequences should not be self-complementary and should not contain G residues which would result in alternative G-quartet structures within the molecule. Representative G-quartet oligonucleotides according to the invention, 15–20 nucleotides in length, are shown in the Examples, but G-quartet oligonucleotides of any length which conform to the general formula of SEQ ID NO:2 are also suitable. The G-quartet oligonucleotide is typically about 14–30 nucleotides in length.

Monitoring the unfolding, linearizing or disruption of a G-quartet structure labeled at each end has several advantages over monitoring linearization of similarly labeled oligonucleotides of the prior art (e.g., self-complementary sequences). First, as the G-quartet is not self-complementary, it unfolds more readily in the presence of the complementary oligonucleotide, providing a more rapid change in fluorescence and a more rapid assay result. Further, multiple G-quartets may be incorporated into a single oligonucleotide to amplify the fluorescent signal and enhance the change in fluorescence intensity in the presence of a complementary sequence. In such multimeric G-quartet molecules the ratio of acceptor to donor fluorophore may be increased to improve donor quenching, thereby providing a greater change in fluorescence intensity in the presence of the complementary sequence.

Many donor/acceptor dye pairs known in the art are useful in the present invention. These include, for example, fluorescein isothiocyanate (FITC)/tetramethylrhodamine isothiocyanate (TRITC), FITC/Texas Red™ (Molecular Probes), FITC/N-hydroxysuccinimidyl 1-pyrenebutyrate (PYB), FITC/eosin isothiocyanate (EITC), N-hydroxysuccinimidyl 1-pyrenesulfonate (PYS)/FITC, FITC/Rhodamine X, FITC/tetramethylrhodamine (TAMRA) and others. The selection of a particular donor/acceptor pair is not critical. It is only necessary that the emission wavelengths of the donor fluorophore overlap the absorption wavelengths of the acceptor, i.e., there must be sufficient spectral overlap between the donor and acceptor to allow fluorescence quenching. P-(dimethyl aminophenylazo) benzoic acid (DABCYL) is a non-fluorescent acceptor dye which effectively quenches fluorescence from an adjacent fluorophore, e.g., fluorescein or 5-(2'-aminoethyl) aminonaphthalene (EDANS). Either the donor or the acceptor may be on either the 5' or 3' end of the G-quartet oligonucleotide. Certain donor/acceptor pairs are exemplified above and in the following Examples, however, others will be apparent to those skilled in the art and are also useful in the invention.

5'-terminal labeling and 3'-terminal labeling methods are also known in the art and may be used to link the donor and acceptor dyes to their respective ends of the G-quartet oligonucleotide. For example, 3'-terminal labeling methods include a) periodate oxidation of a 3'-terminal ribonucleotide followed by reaction with an amine-containing label, b) enzymatic addition of a 3'-aliphatic amine-containing nucleotide using terminal deoxynucleotidyl transferase followed by reaction with an amine-reactive label, and c) periodate oxidation of a 3'-ribonucleotide followed by reaction with 1,6-hexanediamine to provide a 3'-terminal aliphatic amine which can be reacted with an amine-reactive label. Examples of 5'-terminal labeling methods include a) periodate oxidation of a 5'-to-5'-coupled ribonucleotide followed by reaction with an amine-containing label, b) condensation of ethylenediamine with a 5'-phosphorylated polynucleotide followed by reaction with an amine-reactive label, and c) introduction of an aliphatic amine substituent using an aminohexyl phosphite reagent in solid-phase DNA synthesis followed by reaction with an amine-reactive label. Labels may also be linked to synthetic DNA oligonucleotides at specific interior or terminal locations using special aliphatic amine-containing nucleotide phosphoramidite reagents. Selection of an appropriate method for linking the selected labels to the G-quartet oligonucleotide and performing the linking reactions are routine in the art. It is also to be understood that the present description of labels at the 5' and 3' ends of a G-quartet structure is intended to include labels which are near the ends, i.e., not linked to the terminal nucleotides but close enough to the ends that quenching occurs in the G-quartet structure. Linkage of the donor and acceptor is typically within about 2–4 nucleotides of the terminal nucleotide. Only routine testing is required to determine what donor/acceptor pair linkages near the 5' and 3' ends of the G-quartet oligonucleotide provide quenching of donor fluorescence in the folded G-quartet structure. Further, when the G-quartet sequence is contained in or linked to a larger oligonucleotide probe for use as a detector molecule or label (as in Example 3), either the donor or acceptor, or both, may be linked to an internal nucleotide in the probe which is at or near the end of the sequence which forms the G-quartet structure. These linkages may be to nucleotides which are within the sequence which forms the G-quartet structure or they may be to nucleotides which are at or near the end of the G-quartet sequence in the probe portion of the oligonucleotide (i.e., outside of the G-quartet sequence). Such linkages are all considered to be at or near the end of the G-quartet sequence or structure. Routine testing may be employed to determine which nucleotides at or near the ends of the G-quartet are suitable for linking donor fluorophores and acceptor dyes to achieve donor quenching in such probes.

G-quartet oligonucleotides labeled according to the invention may be used in a variety of assays for detection or identification of selected nucleic acid sequences. The essential feature of such assays is that the G-quartet structure is unfolded or linearized in a manner which is dependent upon the presence of the selected nucleic acid sequence. This process results in a detectable increase in donor fluorescence due to decreased quenching. It is not necessary that the donor be totally quenched prior to disruption of the G-quartet, as the assay depends only on a change in donor fluorescence intensity of sufficient magnitude to be detected as an indication of the presence of the selected nucleic acid sequence. While any means which sequence-specifically disrupts the G-quartet structure is useful in the invention, certain examples are provided. Disruption of the structure by unfolding or linearization may be accomplished by hybridization of the G-quartet to the complement of the G-quartet sequence. If the complement of the G-quartet is itself the sequence which is to be detected, or if the selected nucleic acid sequence contains the complement of the G-quartet, an increase in donor fluorescence intensity upon hybridization of the labeled G-quartet may be used to directly detect the selected nucleic acid sequence. If, however, the sequence to be detected does not contain a sequence complementary to the G-quartet other methods must be employed to unfold the G-quartet in a sequence-specific manner. For example, the labeled G-quartet may be linked to the 5'-end of a detector probe which hybridizes to the 3' end of the nucleic acid sequence to be detected or identified such that the G-quartet forms a 5' overhang. Upon hybridization, the selected nucleic acid sequence and the detector probe are made double-stranded by a polymerase using the hybridized segment of the selected nucleic acid sequence as a priming site. Extension of the selected nucleic acid sequence using the detector probe with the G-quartet as a template causes the G-quartet structure to unfold and linearize as the complementary sequence is synthesized through this segment of the detector probe. The resulting increase in donor fluorescence indicates the presence of the sequence to which the detector probe hybridizes. Alternatively, the labeled G-quartet oligonucleotide may be linked to the 5' end of a signal primer as described in published European Patent Application 0 678 582. Following hybridization of the signal primer to the selected nucleotide sequence, extension and displacement produce a single-stranded secondary amplification product which comprises the G-quartet at the 5' end. This secondary amplification product hybridizes to a second amplification primer and extension of the hybridized second amplification primer by polymerase renders the secondary amplification product, including the G-quartet, double-stranded. That is, as the complement of the secondary amplification product is synthesized through the region of the linked G-quartet structure, the G-quartet is unfolded and the distance between the two labels is increased. Enhanced fluorescence intensity of the donor fluorophore indicates the presence of double stranded secondary amplification products and the presence of the selected nucleic acid sequence (i.e., the target sequence being amplified). Of course, in any of the inventive assays a decrease in fluorescence of an acceptor fluorophore may be monitored as an indication of the presence of the selected nucleic acid sequence instead of an increase in donor fluorescence if the acceptor is a fluorophore which responds to increased distance from the donor in this manner.

Unfolding of disruption of the G-quartet structure according to the invention may also be detected or monitored by means of other fluorescence properties which increase or decrease as the proximity of donor and acceptor changes. For example, quenching of the donor decreases its fluorescence intensity but may also produce a decrease in its fluorescence lifetime (i.e., the time between excitation and emission). As fluorescence intensity of the donor increases in the unfolded G-quartet, donor fluorescence lifetime may also increase and be detected as an alternative to detecting decreased donor quenching (increased fluorescence intensity). Similarly, fluorescence polarization may change as the distance between the two dyes changes. The change in molecular volume associated with conversion of the G-quartet oligonucleotide from single-stranded to double-stranded form contributes to changes in fluorescence polarization, but fluorescence polarization may also be influenced by the change in proximity of the two dyes. Changes in fluorescence polarization or anisotropy may therefore also be a useful alternative for monitoring or detecting disruption of the G-quartet.

EXAMPLE 1

Fifteen-mer (GGTTGGTGTGGTTGG, SEQ ID NO:3) and 20-mer (GGTTTTGGTTTTGGTTTTGG, SEQ ID NO:4) G-quartet oligonucleotides and their complements were synthesized by conventional methods. Measurements of the circular dichroism (CD) spectra for the 15-mer and the 20-mer were very similar and differed considerably from both double-stranded and single-stranded DNAs of comparable length which do not assume the G-quartet structure (L. B. McGown, et al. Nov. 1, 1995. *Anal. Chem.* pgs. 663A–668A) This confirmed that both oligonucleotides fold efficiently into G-quartets. The oligonucleotides were labeled at the 5' end with fluorescein (the donor) and at the 3' end with either tetramethylrhodamine (TAMRA) or rhodamine-X (ROX). G-quartet oligonucleotides labeled only at either the 5' or 3' end with fluorescein served as unquenched controls. The 5' fluorescein was attached during oligonucleotide synthesis using the 6-FAM reagent (ABI). At the 3' end, fluorescein was linked by use of a fluorescein derivative immobilized on CPG column material (Glen Research, Sterling, Va.). Dyes other than fluorescein were linked to the 3' end of the oligonucleotide via their NHS esters to aminoalkyl linkers using a similar CPG strategy. The labeled oligonucleotides were purified by removal of unreacted dye with size exclusion chromatography (NAP-5 column, Pharmacia) and by elution through an OPC cartridge (ABI). The concentrations of the labeled oligonucleotides were derived from the calculated absorbance at 260 nm corrected for the dye absorbance at the same wavelength. The fluorescence spectra were analyzed using either an SLM-Aminco 8100 research grade spectrofluorometer or an FPM-1 fluorometer (Jolley Consulting) equipped with filters for fluorescein excitation and emission.

The dye labeled oligonucleotide (2–10 nM) was added to a buffer consisting of 20 mM TRIS acetate, 140 mM NaCl, 5 mM KCl, 1 mM $CaCl_2$, and 1 mM $MgCl_2$ at pH 7.5 at ambient temperature (about 24°–26° C.). The complementary sequence was added in a 1.5-fold or greater molar excess and final measurements were taken when no further changes were seen in the fluorescence spectrum. This typically took less than 30 min. The donor intensity change was determined at the emission wavelength of fluorescein (about 520 nm) with excitation at 485 or 488 nm. The percent quenching was determined by comparison to a similar sequence labeled only with fluorescein at the 5' end. The results are shown in the following Table:

| APTAMER LENGTH | 5'-DONOR DYE | 3'-ACCEPTOR DYE | QUENCHING (%) | INTENSITY INCREASE (Donor Emission) |
|---|---|---|---|---|
| 15-mer | Fluorescein | Rhodamine-X | 25 | 9X |
| 15-mer | Fluorescein | TAMRA | 60 | 5X |
| 15-mer | Fluorescein | Fluorescein | NA | 2.5X |
| 20-mer | Fluorescein | TAMRA | 30 | 2.4X |
| 20-mer | Fluorescein | Fluorescein | NA | 1.7X |

Upon hybridization, readily detectable increases in the intensity of fluorescein fluorescence were observed for all donor/acceptor dye pairs and both oligonucleotides upon hybridization. The fluorescein donor and rhodamine-X acceptor on the 15-mer resulted in the largest increase (9-fold), but the expected decrease in the acceptor (ROX) emission was smaller than predicted (less than 2-fold). This suggests that some of the fluorescence quenching may be due to mechanisms other than Förster energy transfer. The results reported in the Table above show the increase in the emission of the donor. However, with sufficient change, a decrease in the emission of the acceptor could also be used to monitor disruption of the G-quartet upon hybridization. This would give a large effective Stokes shift, as excitation would be at the donor wavelength but emission would be monitored at the wavelength of the acceptor. This configuration would also result in less interference from sample background.

Changes in fluorescence polarization upon hybridization of SEQ ID NO:3 (5' fluorescein, 3' TAMRA) were also monitored under similar experimental conditions. With donor excitation at 475 nm and emission monitored at 585 nm fluorescence polarization increased from 62 to 138 mP upon hybridization of the complement.

EXAMPLE 2

In an experiment similar to Example 1, increasing amounts of the 15-mer complementary oligonucleotide were added to SEQ ID NO:3 labeled at the 5' end with fluorescein and at the 3' end with ROX. The complementary sequence was added at 0.5 molar equivalents, 1.0 molar equivalent, 10 molar equivalents and 30 molar equivalents of SEQ ID NO:3. The absence of the complementary oligonucleotide provided baseline fluorescence readings. After addition of the complementary oligonucleotide the samples were incubated at room temperature for five minutes. The dyes were excited at 485 nm and the emission spectra were recorded. The results are shown in FIG. 1. Emission at 520 nm increased with increasing amounts of the complement: 2-fold (0.5 equivalents), 5-fold (1.0 equivalents), 8-fold (10 equivalents) and 9-fold (30 equivalents). Unfolding of more G-quartets and greater reductions in quenching therefore occur as more of the complementary oligonucleotide hybridizes. This suggests that the method may be semiquantitative, or possibly quantitative, and useful as a means for estimating the amount of a selected nucleotide sequence present in a sample or for comparing relative quantities of the selected sequence in different samples.

EXAMPLE 3

A G-quartet sequence was added to the 5' end of a probe for detection of Chlamydia organisms. The sequence was labeled with 6-FAM at the 5' end and with ROX at T-16 as follows (SEQ ID NO:5):

F-GGTTGGTGTGGTTGGT*CTAGAGTCTTCAAATATCAGA-GCTTTACCTAACAA

F=fluorescein

T*=dT with amino-C6 linker to ROX (Rhodamine X)

The probe was synthesized on an ABI 380B synthesizer with ABI's 6-FAM reagent and the dT C6 amino linker from Glen Research was inserted at the indicated position. Following deprotection the crude oligonucleotide was purified by reverse phase HPLC using a Waters C18 Delta Pak 300 Å C18 3.9×150 mm column using a linear solvent gradient from 2% to 30% acetonitrile in 50 mM TEAA over 30 min. Half of this (0.5 μmole) was dissolved in 100 μL of 100 mM sodium carbonate/bicarbonate buffer at pH 8 and 30 μL of a DMSO solution of 5 mg/60 μL ROX NHS ester (ABI/Perkin Elmer) was added. The resulting mixture was allowed to stand in the dark for 24 hr. at 37° C. and was passed over a column of G-25 SEPHADEX Resin (NAP5, Pharmacia Biotech) eluting with 4 mM TAE (4 mM TRIS acetate, 0.1 mM EDTA, pH 8.0). This product was purified by HPLC as described above. An unlabeled oligonucleotide (SEQ ID NO:6) was synthesized by conventional methods to serve as a target for hybridization of SEQ ID NO:5 and as a primer for extension using SEQ ID NO:5 as a template. This oligonucleotide (TTGTTAGGTAAAGCTCTGATATTTGAAG) was complementary to the 3' end of the probe.

Four 100 μL cuvettes containing 20 nM fluorescent probe, 40 mM KiPO$_4$, 5 mM Mg(OAc)$_2$, 0.2 mM each deoxynucleoside triphosphate, 1.4 mM alpha-thio-dCTP, 5% glycerol and either 0, 0.2, 1.0 or 10 equivalents of target oligonucleotide were prepared and placed in an SLM 8100 fluorometer with the sample chamber preheated to 53° C. Bst polymerase (New England BioLabs, 25 U/100 μL) was added to each sample and the fluorescence intensity was measured over time for all four samples. Excitation was at 484 nm (slits at 4 nm/4 nm) and emission was set at 520 mn (slits at 10 nm/10 nm).

Figure 2:
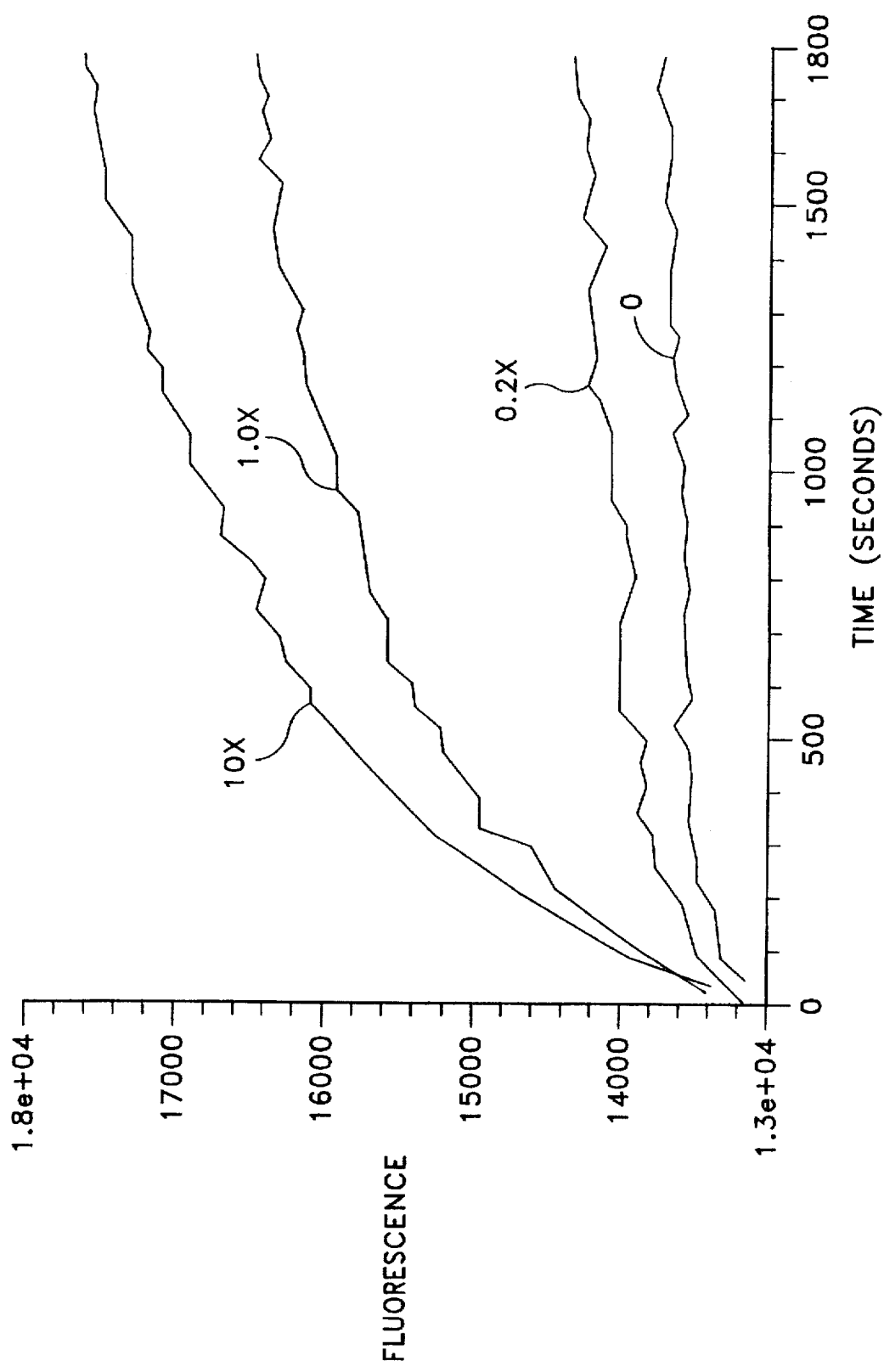
FIG. 2 is a graph illustrating the increase in donor fluorescence when a hybridized primer is extended through a G-quartet, thereby unfolding or linearizing the G-quartet structure and increasing the distance between the donor fluorophore and the acceptor.

The results are shown in FIG. 2. The increase in donor fluorescence in the presence of target indicates unquenching resulting from an increase in the distance between the two fluorophores as the complement is synthesized and the G-quartet is unfolded and linearized. The magnitude of the change in fluorescence increases with increasing amounts of target, indicating at least a semi-quantitative assay. Further, FIG. 2 illustrates that there is a more rapid rate of increase when more target is present. This indicates utility for real-time detection of nucleic acids using primer extension to disrupt the G-quartet, possibly semi-quantitatively, in SDA reactions or other assays based on extension of a hybridized primer.

EXAMPLE 4

A probe for detection of the IS6110 insertion element of *Mycobacterium tuberculosis* linked to a G-quartet at the 5' end was tested in a primer extension assay similar to Example 3. The detector probe was labeled at the 5' end with 6-FAM and with TAMRA at T-16 as follows (SEQ ID NO:7):

F-GGTTGGTGTGGTTGGT*TTATCCGTATGGTGGATAACGT-CTTTCA

F=fluorescein

T*=dT linked to TAMRA

Figure 3:
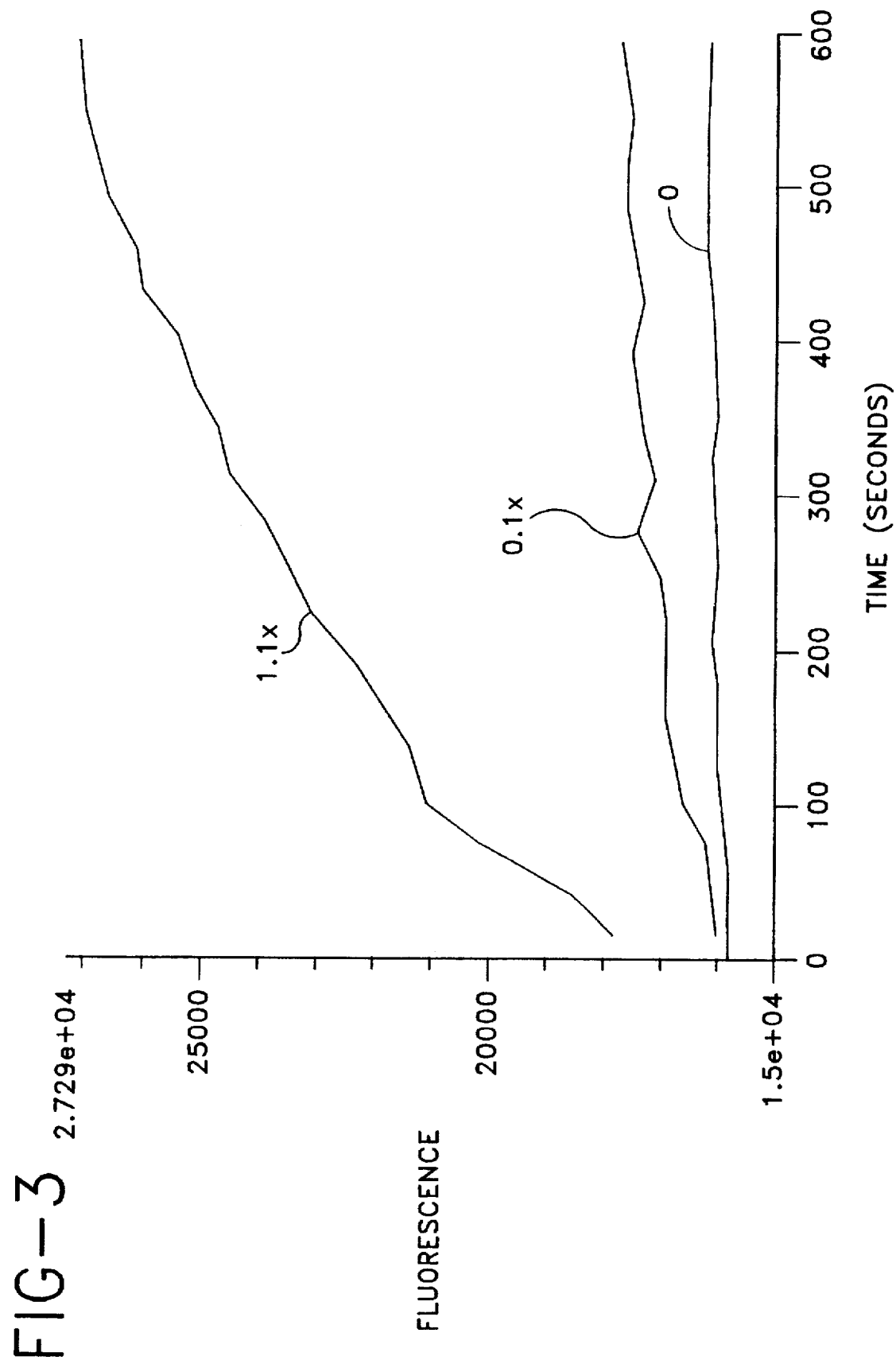
FIG. 3 is also a graph illustrating the increase in donor fluorescence when a hybridized primer is extended through a G-quartet.

The oligonucleotide complementary to the 3' end of the detector probe was SEQ ID NO:8 (GACGTTATCCACCATACGG). The experiment was performed at 55° C. as in Example 3, with 0, 0.1 and 1.1 equivalents of SEQ ID NO:8 present. FIG. 3 shows an increase in donor fluorescence in the presence of target. This is due to the increased distance between the donor and acceptor of the detector probe as the complementary sequence is synthesized using the hybridized target oligonucleotide as a primer. The greater the amount of target present, the greater the magnitude of the increase in fluorescence. Again, a more rapid rate of increase in fluorescence was observed when more target was present. In this experiment the magnitude of the change in fluorescence with a ten-fold increase in target was significantly larger than in Example 3, suggesting that this may be a more sensitive assay system.

Examples 3 and 4 demonstrate the essential feature for use of G-quartets as labels or detector molecules on signal primers in SDA and other amplification reactions, i.e., the ability of an amplification primer to hybridize to a signal primer with a G-quartet at its 5' end and be extended through the G-quartet, thereby disrupting the G-quartet structure and increasing the distance between the donor and acceptor. The decrease in the proximity-dependent interaction between the two labels results in a measurable change in the fluorescence of one or both of the labels. This was demonstrated in an SDA reaction performed generally as described in EP 0 684 315. The amplification reactions were conducted at 55° C., using AvaI as the restriction endonuclease and SEQ ID NO:7 as the signal primer. Genomic DNA of *M. tuberculosis* was added as the target for amplification. The results are shown in FIG. 4. Donor fluorescence remained constant at a low level over time in the control reaction which contained no target. In the amplification reactions containing target (10, 100 or 1000), donor fluorescence increased measurably over time as the target was amplified. These results indicate that the signal primer was extended, displaced and rendered double-stranded as a result of target amplification and that the G-quartet sequence in the signal primer was unfolded as this process occurred. An increase in fluorescence as the G-quartet structure is disrupted in a target amplification-specific manner is therefore a useful method for detecting target amplification. Further, the rate of increase in donor fluorescence intensity is more rapid as the initial amounts of target increases. The rate of increase in donor fluorescence intensity (i.e., the rate of decrease in donor quenching) is therefore at least a semi-quantitative indication of the initial amount of target in the sample and may also be used to compare the relative initial amounts of target contained in multiple samples.

What is claimed is:

1. An oligonucleotide which forms an intramolecular G-quartet structure, the oligonucleotide being labeled with a donor fluorophore and an acceptor, the donor fluorophore and the acceptor selected such that fluorescence of the donor fluorophore is quenched by the acceptor when the oligonucleotide forms the G-quartet structure and quenching of donor fluorophore fluorescence is reduced upon unfolding of the G-quartet structure.

2. The oligonucleotide of claim 1 consisting of SEQ ID NO:2 labeled with the donor fluorophore and the acceptor.

3. The oligonucleotide of claim 1 consisting of SEQ ID NO:3 labeled with the donor fluorophore and the acceptor.

4. The oligonucleotide of claim 1 consisting of SEQ ID NO:4 labeled with the donor fluorophore and the acceptor.

5. The oligonucleotide of claim 1 consisting of SEQ ID NO:5 labeled with the donor fluorophore and the acceptor.

6. The oligonucleotide of claim 1 consisting of SEQ ID NO:7 labeled with the donor fluorophore and the acceptor.

7. The oligonucleotide of claim 1 wherein the donor fluorophore is fluorescein and the acceptor is selected from the group consisting of tetramethylrhodamine, Texas Red™, N-hydroxysuccinimidyl 1-pyrenebutyrate, eosin, N-hydroxysuccinimidyl 1-pyrenesulfonate (PYS), Rhodamine X, tetramethylrhodamine and p-(dimethylaminophenylazo) benzoic acid.

8. The oligonucleotide of claim 7 wherein the donor fluorophore is fluorescein and the acceptor is Rhodamine-X.

9. A method for detecting or identifying a selected nucleic acid comprising:

a) providing an oligonucleotide probe comprising an intramolecular G-quartet structure and a sequence complementary to the selected nucleic acid, the oligonucleotide being labeled with a donor fluorophore and an acceptor such that fluorescence of the donor fluorophore is quenched by the acceptor when the oligonucleotide forms the G-quartet structure, and quenching of donor fluorescence is reduced upon unfolding of the G-quartet structure;

b) contacting the oligonucleotide probe with a nucleic acid sample, whereby if the selected nucleic acid is present the oligonucleotide probe binds to the selected nucleic acid and is rendered double-stranded, thereby unfolding the G-quartet structure and reducing quenching of donor fluorescence; and c) detecting a change in fluorescence; thereby detecting or identifying the selected nucleic acid.

10. The method of claim 9, wherein an increase in donor fluorescence is detected.

11. The method of claim 9, wherein the acceptor is a fluorophore and a decrease in acceptor fluorescence is detected.

12. The method of claim 9 wherein the oligonucleotide is rendered double-stranded by hybridization to a complementary sequence.

13. The method of claim 9 wherein the oligonucleotide is rendered double-stranded by synthesis of its complement using the oligonucleotide as a template.

14. The method of claim 9 wherein the oligonucleotide consists of SEQ ID NO:2 labeled with the donor fluorophore and the acceptor.

15. The method of claim 9 wherein the oligonucleotide consists of SEQ ID NO:3 labeled with the donor fluorophore and the acceptor.

16. The method of claim 9 wherein the oligonucleotide consists of SEQ ID NO:4 labeled with the donor fluorophore and the acceptor.

17. The method of claim 9 wherein the oligonucleotide consists of SEQ ID NO:5 labeled with the donor fluorophore and the acceptor.

18. The method of claim 9 wherein the oligonucleotide consists of SEQ ID NO:7 labeled with the donor fluorophore and the acceptor.

19. The method of claim 9 wherein the donor fluorophore is fluorescein and the acceptor is selected from the group consisting of tetramethylrhodamine, Texas Red™, N-hydroxysuccinimidyl 1-pyrenebutyrate, eosin, N-hydroxysuccinimidyl 1-pyrenesulfonate (PYS), Rhodamine X, tetramethylrhodamine and p-(dimethylaminophenylazo) benzoic acid.

20. The method of claim 9 wherein the nucleic acid sequence to be detected or identified is a product of a nucleic acid amplification reaction.

21. The method of claim 20 wherein the nucleic acid sequence to be detected is the amplification product of an SDA reaction.

22. A method for detecting or identifying a selected nucleic acid comprising:

a) providing an oligonucleotide probe comprising an intramolecular G-quartet structure and a sequence complementary to the selected nucleic acid, the oligonucleotide being labeled with a donor fluorophore and an acceptor such that unfolding of the G-quartet structure increases the distance between the donor fluorophore and acceptor;

b) contacting the oligonucleotide probe with a nucleic acid sample, whereby if the selected nucleic acid is present the oligonucleotide probe binds to the selected nucleic acid and is rendered double-stranded, thereby unfolding the G-quartet structure and increasing the distance between the donor fluorophore and acceptor; and c) detecting a change in a fluorescence property associated with the increased distance between the donor fluorophore and the acceptor, thereby detecting or identifying the selected nucleic acid.

23. The method of claim 22 wherein the fluorescence property is selected from the group consisting of fluorescence intensity, fluorescence lifetime, fluorescence polarization and fluorescence anisotropy.

* * * * *